United States Patent [19]

Buzza

[11] 3,997,420
[45] Dec. 14, 1976

[54] AUTOMATIC ANALYZER

[75] Inventor: Edmund E. Buzza, Fullerton, Calif.

[73] Assignee: Beckman Instruments, Inc., Fullerton, Calif.

[22] Filed: Feb. 18, 1975

[21] Appl. No.: 550,271

Related U.S. Application Data

[63] Continuation of Ser. No. 125,770, March 18, 1971, abandoned.

[52] U.S. Cl. .................. 204/195 P; 204/195 F; 204/195 G; 204/195 M; 324/30 R
[51] Int. Cl.[2] .................................. G01N 27/46
[58] Field of Search ............. 204/1 T, 195 R, 195 P, 204/195 F, 195 G, 195 M

[56] References Cited

UNITED STATES PATENTS

| | | | |
|---|---|---|---|
| 1,944,738 | 1/1934 | Grebe et al. | 204/195 F |
| 3,151,052 | 9/1964 | Arthur et al. | 204/195 F |
| 3,424,664 | 1/1969 | Severinghaus | 204/195 G |
| 3,505,195 | 4/1970 | Nielsen et al. | 204/195 P |
| 3,556,950 | 1/1971 | Dahms | 204/195 R |
| 3,658,679 | 4/1972 | Stansell et al. | 204/195 G |
| 3,681,205 | 8/1972 | Ducksbury et al. | 204/195 G |

*Primary Examiner*—T. Tung
*Attorney, Agent, or Firm*—R. J. Steinmeyer; R. R. Meads

[57] ABSTRACT

An apparatus for automatically performing blood chemistry analyses and in particular the determination of the pH, $PCO_2$ and $PO_2$ of blood. The apparatus employs a flow cell having pH, $PCO_2$ and $PO_2$ measuring electrodes mounted therein adjacent to a sample passage extending through the cell. Sample is collected in a conventional syringe. The needle of the syringe is removed and the syringe cylinder is attached to the flow cell adjacent to the inlet end of the sample passage. Means are provided for automatically driving the plunger of the syringe into the cylinder to convey the sample through the sample passage. A wash solution is then conveyed through the passage to discharge the sample therefrom and thereafter a calibration solution is conveyed through the passage which permits simultaneous calibration of the pH, $PCO_2$ and $PO_2$ electrodes. A unique construction of the flow cell and means for mounting the measuring electrode therein allows the use of a single reference electrode which is common to each of the measuring electrodes. Means are also disclosed for allowing flushing of a capillary passage in the flow cell which forms a liquid junction between the reference electrode and the sample in the sample passage.

3 Claims, 13 Drawing Figures

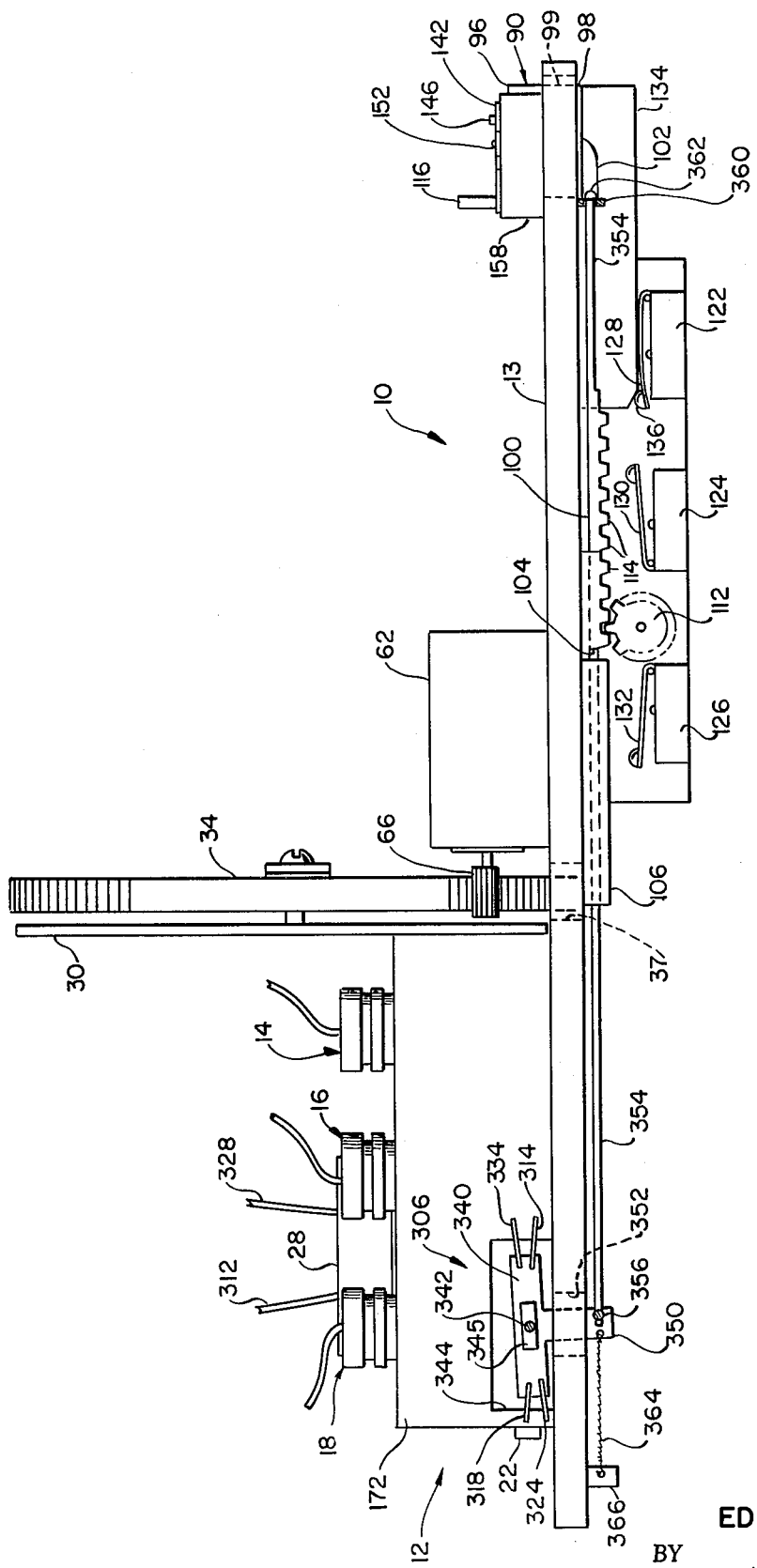

INVENTOR.
EDMUND E. BUZZA
BY
Thomas L. Peterson
ATTORNEY

AUTOMATIC ANALYZER

This is a continuation of application Ser. No. 125,770, filed Mar. 18, 1971, now abandoned.

BACKGROUND OF THE INVENTION

1. Field of the Invention

The present invention relates generally to an automated analyzer and, more particularly, to an analyzer capable of automatically performing blood chemistry determinations and analyses of other biological and biochemical liquids and gases.

2. Description of the Prior Art

Various apparatus are presently available to make electrochemical measurements, such as potentiometric and polarographic measurements, on small liquid samples, which for practical purposes in the biological and biochemical field means sample volumes between 10 microliters and 1000 microliters. Examples of potentiometric measurements, which can be of interest to make in such small samples, are the determination of pH and $PCO_2$, the latter being the partial pressure of carbon dioxide. An example of a polarographic measurement is the determination of $PO_2$, the partial pressure of oxygen.

The determination of the parameters of pH, $PCO_2$ and $PO_2$, in so-called microvolumes of blood is most important in medicine. From the direct measurement of pH and $PCO_2$ the determination of $CO_2$ content, bicarbonate and buffer base can be readily obtained using the Hastings-Singer or similar nomograms. In addition, blood oxygen saturation can be determined quickly from the direct measurement of pH and $PO_2$ and the use of oxygen disassociation curves or nomograms. These measurements are particularly useful to cardio-pulmonary specialists and have been a valuable aid in surgery, pulmonary function studies, cardiac catheterization, anesthesia studies and in clinical laboratories for determination of "acid-base" imbalance.

In view of the increasing importance in research and clinical medicine for making the aforementioned measurements, particularly with respect to microvolumes of blood, a need has arisen for rapid, reliable and economical instrumentation which would allow such analyses to be performed automatically. Presently available blood chemistry analyzers have several drawbacks, an important one being that the pH measuring electrode system is separate from the $PCO_2$ and $PO_2$ blood measuring systems so that a single sample must be divided and introduced into each system independently or sequentially. Moreover, the operation of presently available blood chemistry analyzers require considerable operator attention and technical skill. One particular blood chemistry analyzer is claimed to be fully automatic, but in actuality is semi-automatic inasmuch as the sample must be held manually in a syringe or other sealed container at the inlet port of the apparatus while a vacuum pump draws the sample through the apparatus for analysis. In addition, while means are provided for automatically circulating a wash solution through the major portion of the flow passages in the apparatus, the operator must hold a bottle of wash solution at the sample inlet port to assure that all sample will be cleaned from the inlet end of the sample passage to avoid any carryover of sample into the analysis cell from one test to another. The operator must also observe lights appearing on the instrument panel of the analyzer to determine when the sample and wash solution containers should be introduced to and withdrawn from the sample inlet port thus prohibiting the operator from performing other tasks in the laboratory. In addition, the pH electrode and the $PCO_2$ and $PO_2$ sensors must be calibrated separately since a buffer solution is utilized to calibrate the pH electrode and a humidified gas is utilized as the calibration media for the gas measuring sensors. In view of the foregoing, it can be appreciated that there is a need for a more automated apparatus for performing blood chemistry analyses, preferably one which will require virtually no operator attention and will overcome some if not all of the disadvantages discussed above in connection with the presently available systems. The purpose of the present invention is to provide such an apparatus.

SUMMARY OF THE INVENTION

According to the principal aspect of the present invention, there is provided an apparatus for automatically analyzing biological fluids and, in particular, the determination of pH, $PCO_2$ and $PO_2$ of microvolumes of blood. The apparatus includes a sample flow cell in which there are mounted a plurality of measuring electrodes adapted to contact sample flowing through a sample passage extending through the cell. Sample is introduced into the flow cell by attaching a syringe containing the sample to the flow cell adjacent to the inlet end of the sample passage. Means are provided for automatically driving the plunger of the syringe into the syringe cylinder to positively displace sample from the cylinder and to cause the sample to flow through the sample passage. Means are also provided for automatically conveying a wash solution through the sample passage and into the syringe cylinder to assure that all sample is flushed from passages within the flow cell, including the inlet end of the sample passage. Means are also provided for automatically circulating a calibration solution through the sample passage which allows simultaneous calibration of all the measuring electrodes mounted in the flow cell. The apparatus requires no operator attention other than merely attaching the sample-containing syringe to the inlet of the flow cell. All other operations are performed automatically in a rapid and reliable manner.

According to another aspect of the invention, there is provided means for mounting the pH, $PCO_2$ and $PO_2$ measuring electrodes in the flow cell in such a manner that only a single reference electrode is required which is common to each of the measuring electrodes. This feature allows the use of a large reservoir of reference elecrolyte which will permit replenishment of electrolyte in the $PCO_2$ and $PO_2$ electrodes without disassembling the electrodes from the flow cell, thereby considerably reducing operator maintenance of the apparatus.

BRIEF DESCRIPTION OF THE DRAWINGS

FIG. 4 is an elevational view of the other side of the apparatus illustrated in FIG. 1;

DESCRIPTION OF THE PREFERRED EMBODIMENT

Figure 1:
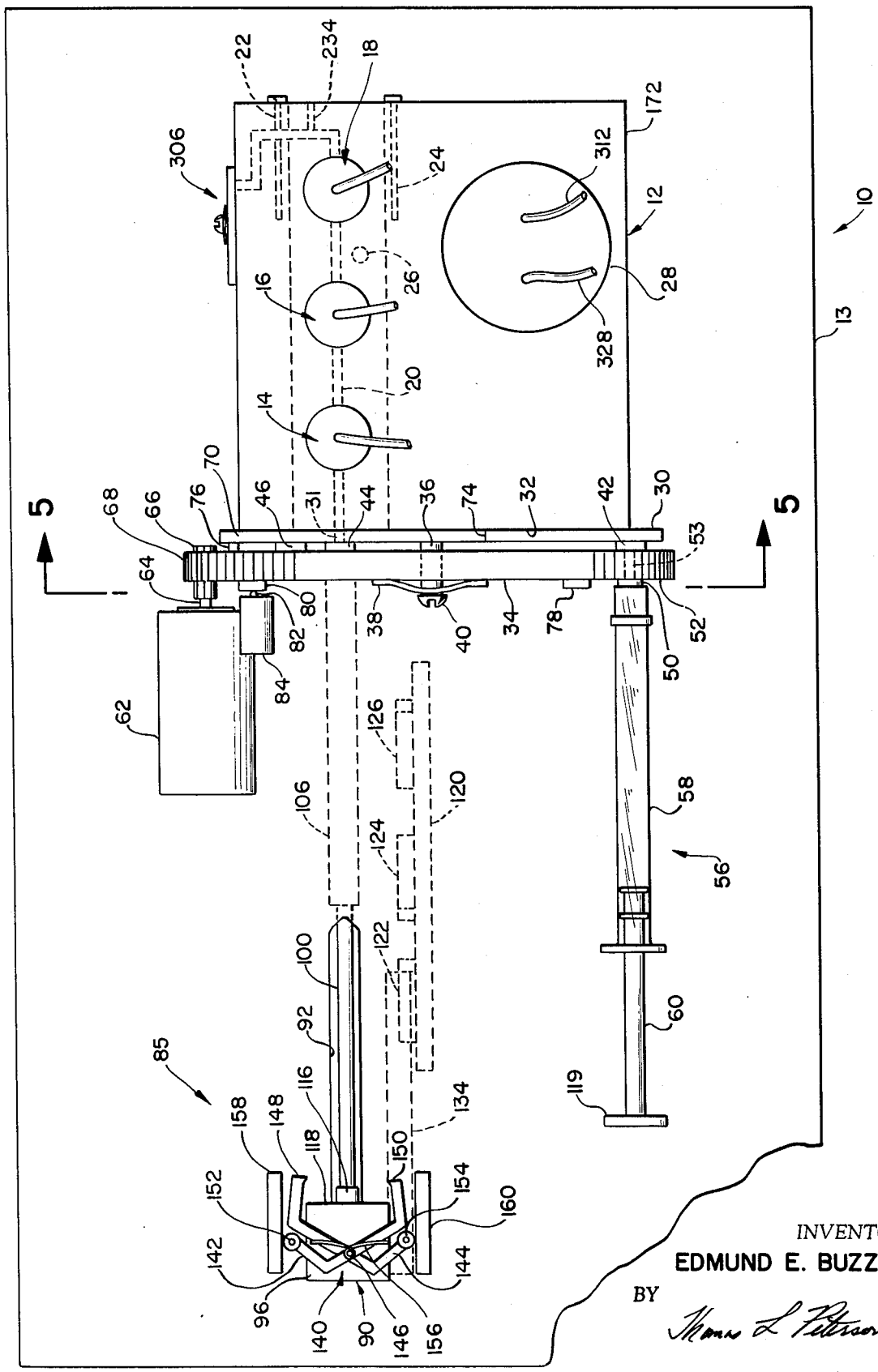
FIG. 1 is a top plan view of the major portion of the apparatus of the present invention showing the sample syringe in the position it would take when initially attached to the apparatus.

Referring now to the drawings in detail, the apparatus of the invention, generally designated 10, comprises a flow cell assembly 12 mounted on top of a base 13. A plurality of electrochemical measuring electrodes 14, 16 and 18 are mounted in the flow cell 12 with their sensing ends positioned to contact sample flowing through a sample passage 20 which extends through the cell. Two heaters 22 and 24 are mounted in the flow cell to heat the same. A temperature sensing element 26, preferably a thermistor, is mounted in the cell and connected together with the heaters 22 and 24 into a suitable control circuit, not shown, to maintain the flow cell at a substantially constant temperature, preferably 37° C for blood analysis. A vessel 28 containing a calibration solution is mounted in the flow cell 12 so that the calibration solution will be maintained at essentially the same temperature as the sample passing through the passage 20.

A circular plate 30 is mounted on the front face 32 of the flow cell. A bore 31 extending through plate 30 is coaxial with sample passage 20. A circular disc 34 is mounted for rotation on a screw 36 in front of the plate 30. The lower portion of disc 34 extends into a vertical slot 37 cut in the base 13. A leaf spring 38 is disposed between the head 40 of the screw and the disc 34 to urge the disc toward the plate 30.

Figure 7:
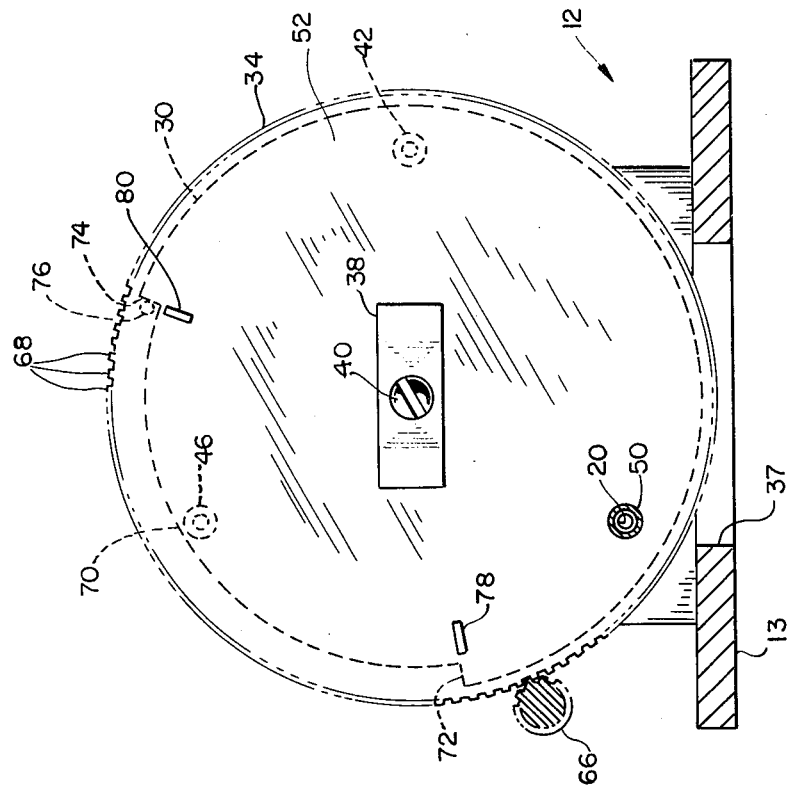
FIG. 7 is a vertical sectional view taken along line 7—7 of FIG. 6.
Figure 5:
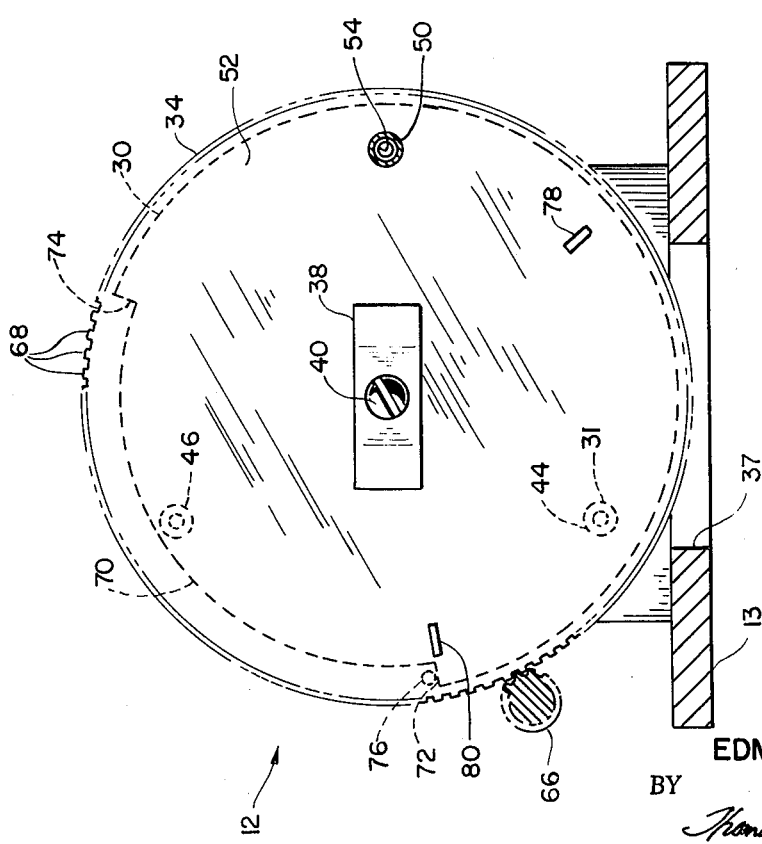
FIG. 5 is a vertical sectional view taken along line 5—5 of FIG. 1.

As best seen in FIGS. 1, 5 and 7, three O-rings 42, 44 and 46 are angularly spaced 120° apart about the outer periphery of the plate 30 and at an equal distance from the center of rotation of disc 34. These O-rings are press fitted into annular grooves, not shown, provided in the front face of the plate 30. The O-rings provide a three point suspension for maintaining the circular disc 34 coplanar with the plate 30. It is seen that the O-ring 44 is coaxial with bore 31 in plate 30. Hence, when disc 34 is positioned as shown in FIGS. 1 and 5, the disc together with O-ring 44 provided a sealed closure for the inlet end of sample passage 20.

A Luer-lock fitting 50 is mounted on the forwad face 52 of the disc 34. The fitting is coaxial with a passage 53 which extends through the disc. Such passage is in alignment with the O-ring 42 when the disc 34 is in the position shown in FIGS. 1 and 5. Thus, in such position of disc 34, the O-ring 42 and plate 30 provide a sealed closure for one end of passage 53.

The fitting 50 is provided for permitting the rapid attachment of a syringe, generally designated 56, to the disc 34. The syringe may be of the standard commercially available disposable type in which blood is collected directly from the subject. After withdrawing blood from the subject, the syringe needle (not shown) is removed and the cylinder 58 of the syringe is attached to the Luer-lock fitting 50. At this time, the plunger 60 of the syringe is in a retracted position as shown in FIG. 1. Thus, by the use of the syringe 56, there is no necessity for transferring sample to a specialized container particularly designed for introducing sample into the flow cell of the apparatus.

Figure 2:
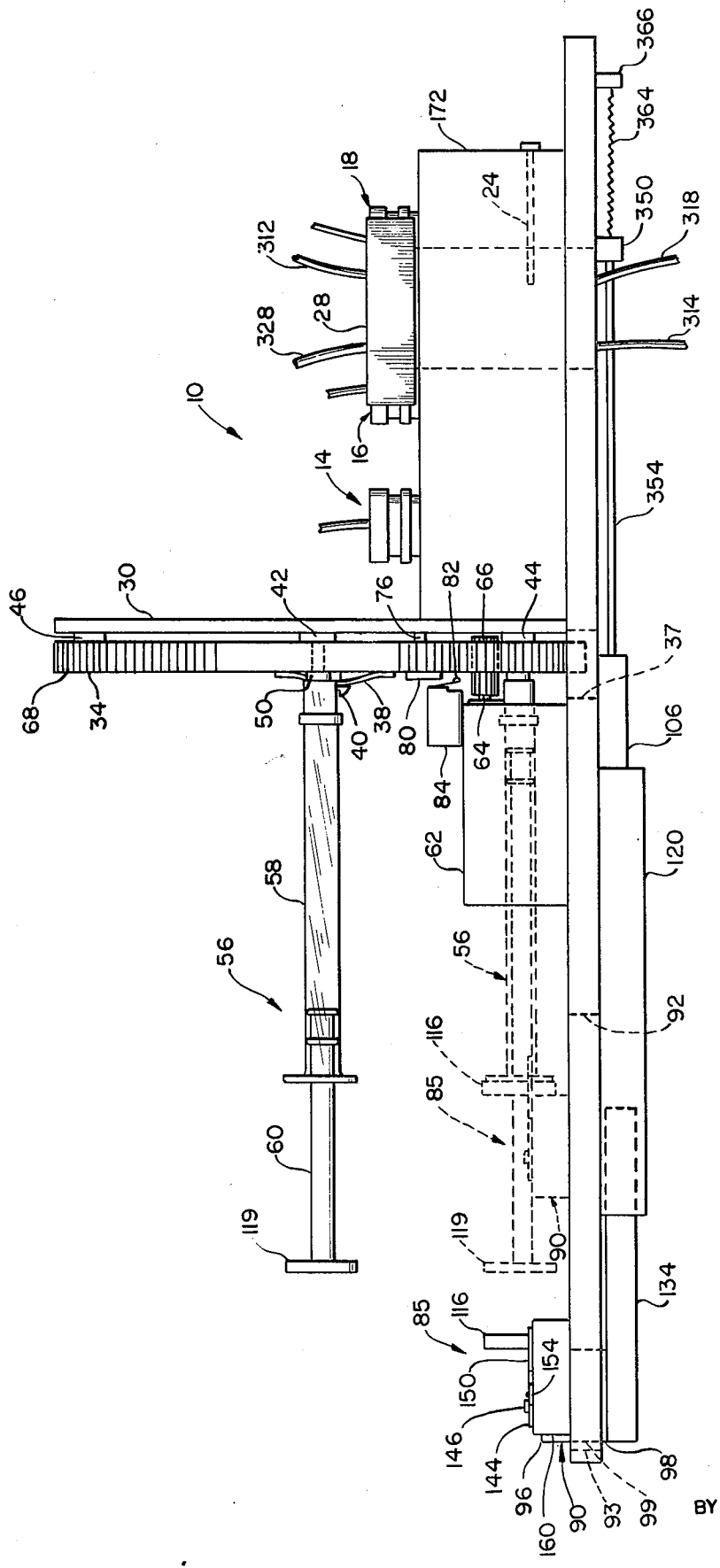
FIG. 2 is an elevational view of one side of the apparatus illustrated in FIG. 1.
Figure 6:
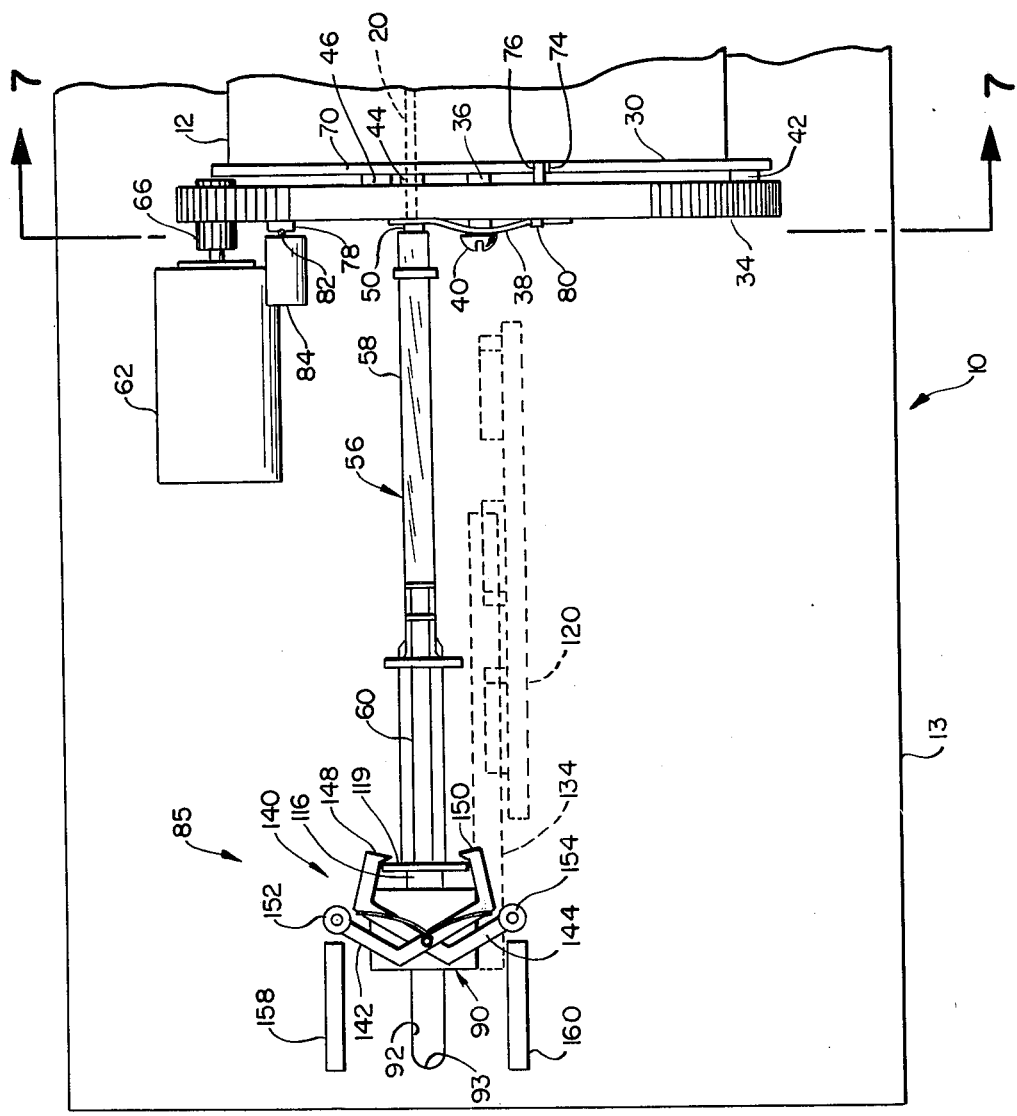
FIG. 6 is a fragmentary top plan view similar to FIG. 1 but showing the sample syringe in the position it would take after being aligned with the sample passage in the flow cell and being initially engaged by the syringe drive.

In order to transfer sample from the syringe cylinder 58 into the passage 20 of the flow cell, it is necessary to rotate the disc 34 120° so as to align the syringe with the sample passage as shown in FIG. 2 in phantom lines and in FIG. 6. This is accomplished by providing a reversible motor 62 having a shaft 64 carrying a gear 66 which engages gear teeth 68 formed on the outer surface of the disc 34. An arcuate slot 70 is cut in the outer periphery of the plate 30 as best seen in FIG. 5. The ends 72 and 74 of the slot are spaced apart 120° corresponding to the angular spacing between the O-rings 42, 44 and 46. A pin 76 fixed to the disc 34 extends rearwardly into the slot 70. A pair of switch actuating tabs 78 and 80 are spaced apart 120° on the front face 52 of the disc 34. These tabs are positioned to contact the actuating arm 82 of a microswitch 84 monted on top of the motor 62 when the tabs are brought into alignment with the arm 82. Engagement of the tabs with the switch arm 82 opens the microswitch 84 and thereby de-energizes the motor 62.

After the operator has attached the sample filled syringe 56 to the Luer-lock fittin 50, he energizes a start switch P1 (seen in FIG. 13) which overrides the microswitch 84 and energizes the motor 62. The motor shaft 64 at this moment will rotate in a counterclockwise direction as viewed in FIG. 5 to effect clockwise rotation of the disc 34. The disc will continue rotating until it reaches the position illustrated in FIG. 7 whereupon the tab 78 will engage switch actuating arm 82 to de-energize the motor 62 and almost simultaneously the pin 76 carried by the disc will engage the end 74 of the slot 70 in the plate 30. The end 74 of slot 70 provides a positive stop that assures that the disc 34 will be exactly positioned so that the syringe 56 is in alignment with the sample passage 20. By a suitable control circuit, to be described in detail later in connection with FIG. 13, a syringe drive mechanism 85 will be energized to force the plunger 60 of the syringe 56 into the cyllinder 58 to positively displace the sample from the cylinder and introduce the same at a constant rate of velocity and minimal pressure through the sample passage 20. As will be appreciated, reversing the rotation of the motor shaaft 64 will effect counterclockwise rotation of the disc 34 until the disc returns to its original position as illustrated in FIG. 5 whereupon the tab 80 will engage switch actuating arm 82 to open the microswitch 84 thereby de-energizing the motor 62 and the pin 76 will engage the end 72 of slot 70.

By employing a conventional syringe for supplying sample to the flow cell 12 of the present invention, essentially anaerobolic transfer of sample is achieved.

Only a minute surface area of the sample is exposed to the atmosphere during the period that the syringe needle is withdrawn from the cylinder 58 and the cylinder is attached to the fitting 50. While the syringe 56 is in the position illustrated in FIGS. 1 and 5, the sample is sealed from the outside environment by means of the O-ring 42. During the period that the disc 34 is rotated to bring the syringe into alignment with sample passage 20, again only a minute surface area of the sample at the tip of the syringe is exposed to the atmosphere. Thus, the exposure of the sample to the atmosphere occurs for only a matter of a few seconds and then only a minute area of the sample is exposed. This is in contrast to prior art systems which employ vacuum pumps for drawing sample from a sample container in which case the container must be open during the entire period that sample is fed into the analysis cell and a large area of sample is exposed to the atmosphere, with the result that the sample composition and particularlly the $PO_2$ of the sample may change from its actual value.

The drive mechanism 85 for the syringe 56 includes a block 90 which is slideable in a longitudinally extending slot 92 formed in the base 13. This slot is in alignment with the sample passage 20 in flow cell 12. The block is normally positioned adjacent to the rear end 93 of the slot to introduce sample into the sample passage. The block 90 includes an upper part 96 sliding on the upper surface of the base 13 and a lower part 98 positioned below the base. An intermediate part 99 interconnects the uppe and lower parts 96 and 98, respectively, and is dimensioned to slide in the slot 92. A longitudinally extending rack 100 iss fixedly attached at its rear end 102 to the bottom of the lower part 98 of block 90. The forward end 104 of the rack is slideably engaged in a rack guide 106 which is fixedlymounted to the bottom of the base 13 in alignment with slot 92.

Figure 3:
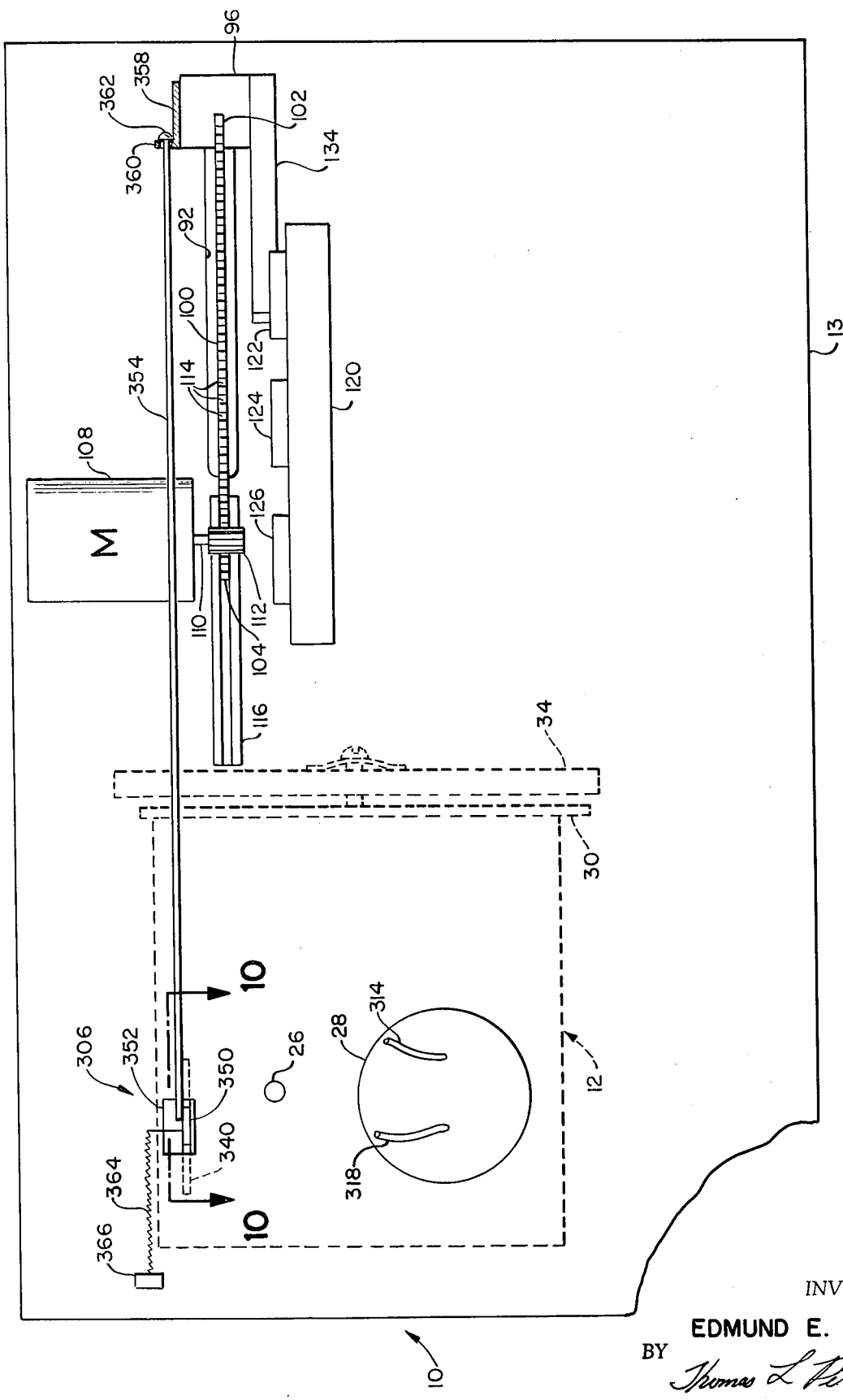
FIG. 3 is a bottom plan view of the apparatus illustrated in FIG. 1.

As best seen in FIG. 3, a constant speed reversible motor 108 is fixedly mounted to the bottom of the base 13. The shaft 110 of the motor 108 carries a pinion gear 112 which engages the teeth 114 formed on the bottom of the rack 100. The motor 108 has been omitted from FIG. 4 of the drawings in order that the other parts illustrated therein may be more clearly seen.

An upstanding post 116 is mounted on the forward face 118 of the block 90 of the syringe drive mechanism. The post is of a sufficient height so as to engage the circular head 119 of the syringe 56 when the syringe is positioned in alignment with sample passage 20 in flw cell 12 as shown in phantom lines in FIG. 2 and in full lines in FIG. 6. It can be appreciated that upon energization of the motor 108 to drive the pinion 112 in a counterclockwise direction as viewed in FIG. 4, the rack 100 and therefore the block 90 will be moved toward the cell 12 whereupon the post 116 will engage the head 119 of the syringe thereby driving the plunger 60 into the syringe cyllinder 58. Since the motor 108 is a constant speed motor, the aforementioned syringe drive will introduce the sample from the syringe 56 into the sample passage 20 at a constant rate under repeatable conditions of velocity and minimal pressure. Thus, the syringe drive 85 and the syringe plunger 60 constitute means for positively displacing sample from the syringe cylinder 58 into the sample passage 20 of flow cell 12. By positively displacing or forcing the sample from the syrige 56 into the sample passage, the introduction of air or gas bubbles into the flow cell is avoided. This constitutes a substantial advantage over those prior art analyzers employing a suction pump for drawing sample from a sample container through a flow cell in which case airor gas bubbles are created in the sample. This will result in a lack of equilibrium being reached between the sample and the measuring electrodes or a high impedance or discontinuity of sample with the reference junction in a pH measuring cell. Moreover, the syringe drive mechanism of the present invention avoids sudden pressure differentials, either positive by too rapid an injection or negative by sucking the sample from a syringe by a vacuum pump. These pressure differentials could cause discontinuities in reference junctions or contamination of the junction resulting in junction potential offsets when calibrating with buffer solutions. Negative pressures would also be detrimental to the functioning of membrane covered measuring electrodes as are employed in the flow cell 12 of the present invention as will be seen later. Thus, the sample introducing means of the present invention constitutes a substantial advantage both in its features of automation and repeatability in operation, as well as superior performance over previous sample introduction mechanisms.

It will be seen that an elongated plate 120 is fixed to the bottom of base 13. The plate extends in the same direction as slot 92 and is spaced therefrom. The plate carries three normally open mmicroswitches 122, 124 and 126 provided with pivotally mounted actuating arms 128, 130 and 132, respectively. A longitudinally extending switch actuating rod 1334 is affixed to the bottom of lower plate 98 of the block 90. This rod is positioned in such a manner that its forward beveled end 138 will engage the switch actuating arms 128, 130 and 132 in sequence as the block 90 is deiven by the motor 108 toward the cell 12. The engagement of the rod 134 with switch arms 128 and 130 and 132 will affect various functions of the operation of the apparatus 10 as will be seen later.

There is provided on the block 90 of the syringe drive mechanism 85 a latching mechanism 140 which latches onto the head 119 of the syringe 56 after the syringe drive engages the head. As best seen in FIG. 1, the latching mechanism 140 comprises a pair of arms 142 and 144 pivotally mounted on block 90 by means of a vertically extending shaft 146. Inwardly extending fingers 148 and 150 are formed on the forwardly extending portions of arms 142 and 144, respectively. Rollers 152 and 154, respectively, are rotatably mounted on the opposite ends of the arms 142 and 144. A spring 156 which is wound about the shaft 146 is bent downwardly at its opposite ends to engage the arms 142 and 144 to urge the fingers 148 and 150 toward each other. A pair of longitudinally extending parallel roller guides 158 and 160 are mounted on base 13 on opposite sides of the slot 92 adjacent to its rear end 93. These guides are engaged by the rollers 152 and154 when the block 90 is in its normal rearward position in slot 92 thereby restraining the fingers 148 and 150 from moving toward each other under the influence of the spring 156. The shape and dimensions of the arms 142 and 144 and the spacing between the roller guides 158 and 160 are such that when the rollers 152 and 154 engage the guidess, the fingers 148 and 150 will be spaced apart a distance greater than the diameter of syringe head 119. When the block 90 moves forwardly so that the piost 116 engages the syringe head and the rollers 152 and 154 no longer engage the guide 158 and 160, respectively, the spring 156 will cause the fingers 148 and 150 of the latching mechanism to move toward each other as best seen in FIG. 6 to latch about the syringe head. As the block 90 continues its forward movement to introduce sample from th syringe 56 into the flow cell, as seen in phantomlines in FIG. 2, and during return of the block toward its rearward position in the slot 92, the fingers 148 and 150 will remain engage to the syringe head 119 so that the plunger 60 will be withdrawn from the syringe cylinder 58 upon rearward movement of block 90. As will appear later, the withdrawal of the plunger 60 will cause wash solution circulating in sample passage 20 of theflow cell to be drawn into the syringe cylinder 58 thus ensuring that all passages in the flow cell contacted by the sample, including the passages 31 and 53, will be cleansed by the wash solution. As the block 90 returns to its rearward position in slot 92, the rollers 152 and 154 will agains engage the guides 158 and 160, respectively, thereby spreading the forward ends of arms 142 and 144 to retract the fingers 148 and 150 from the syringe head 119. Thus, the latching mechanism 140 and syringe drive associated therewith serves to engage the syringe plunger in any initial position, thereby allowing different size syringes to be utilized in the apparatus, and also serves to pull the plunger back and release it at the same point each time when the plunger is in its maximum outward or retracted position.

Figure 8:
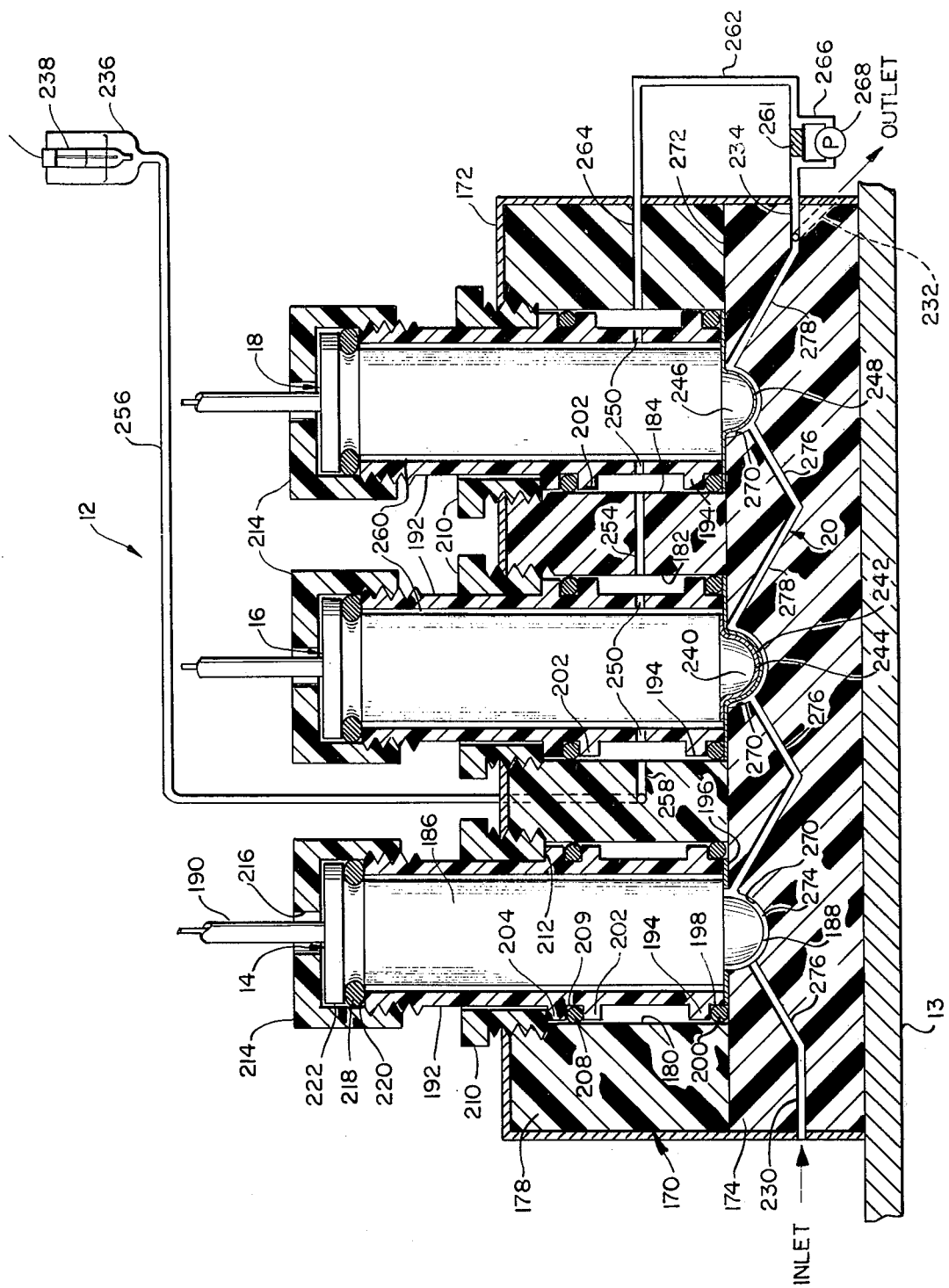
FIG. 8 is a vertical sectional view through the flow cell of the apparatus of the present invention, with the reference electrode and connections thereto from the flow cell being shown schematically.

Reference is now made to FIG. 8 of the drawings which shows in detail the construction of the flow cell 12 of the present invention. The cell includes a body 170 formed of a suitable nonconductive material, such as Lucite, which is disposed within a metal housing 172. The body 170 is divided into two sections, a lower section 174 and upper section 178. These two sections are fixedly secured together in any suitable manner. Three spaced vertical bores 180, 182 and 184 are provided in te upper section 178 of the body. Each of these bores is adapted to receive one of the measuring electrodes 14, 16 or 18. Obviously a fewer or greater number of bores may be provided in the body depending upon the number of anaoyses which is desired to be performed on the sample in question.

The electrode 14 is preferably a pH sensitive electrode comprising a glass tube 186 closed at its lower end with a convex sensing barrier 188 in the form of a hydrogen ion sensitive glass bulb, as well known in the art. The tube 186 holds a suitable electrolyte solution in which there is immersed an internal half cell (not shown) which is connected to a cable 190 that extends from the top of the tube.

Almost identical means are provided for mountig the measuring electrodes in the respective bores 180, 182 and 184. Therefore, such meas will be described in detail only with respect to sensing electrode 14. Corresponding elements of the mounting means for the other measuring electrodes will be designated by like reference characters. The mounting means for electrode 14 includes a cylindrical sleeve 192 which surrounds the tube 186 of the electrode. An annular flange 194 is formed on the sleeve adjacent to but spaced from its lower end 196 to provide an annular groove 198 for receiving an O-ring 200. Two additional annular flanges 202 and 204 are formed on the sleeve above the flange 194 to define therebetween another groove 206 which receives a secnod O-ring 208. A retaining nut 210 is threadedly mounted in the bore 180. The bottom 212 of the nut 210 engages the flange 204 so that threading of the nut 210 into the bore wil firmly secure the sleeve 192 within the bore and compress the O-ring 200 to provide a good seal between the exterior of the lower end of the sleeve and the interior thereof. A cap 214 is threadedly engaged on the upper end of the sleeve 192. A central aperture 216 is provided in the cap through which the cable 190 extends. An O-ring 218 is positioned between the upper end 220 of the sleeve 192 and an outwardly extending annular flange 22 at the upper end of the electrode 14. Thus, upon threading of the cap 214 onto the sleeve 192, the O-ring 220 will be compressed to provide a complete seal between the upper ends of the sleeve and the electrode.

The sample passage 20 of the flow cell is located in the lower section 174 of body 170. Sample is introduced by the syringe 56 into the inlet end 230 of the sample passage while the outlet end 232 is open to waste. An open capillary liquid junction 234 is connected at one end tothe sample passage 20 adjacent to the outlet end 232 and at the other end to suitable conduits and passages, which will be described in detail later, to an electrolyte reservoir 236 in whichthere is positioned a conventional electrochemical reference electrode 238, thereby completing the pH measuring system. The reference electrode may be either a standard calomel electrode or silver-silver chloride electrode. The reference electrode and reservoir 236 are positioned remotely from th measuring electrode and therefore may either be mounted on the base 13 or elsewhere as desired.

The measuring electrodes 16 and 18 are preferably $PCO_2$ and $PO_2$ measuring electrodes. The conventional electrochemical sensor for measuring $PCO_2$ comprises a potentiometeric pH glass electrode and a reference electrode mounted in the same body, joined by a bicarbonate solution, and separated from the sample by means of a gas permeable essentially ion impermeable membrane, such as polyethylene, silicone rubber or polytetrafluoroethylene [that is, Teflon]. Carbon dioxide in the sample being analyzed will diffuse through the membrane and react with the bicarbonate electrolyte to alter the hydrogen ion activity thereof. The change in hydrogen ion activity of the electrolyte results in a change in thepotential difference between the electrodes which is a measure of the partial pressure of carbon dioxide in the sample. The conventional electrochemcal sensor for measuring partial presure of oxygen is a polarographic cell including a metal cathode and an anode (which will be referred to hereinafter as a reference electrode) mounted in the same body, joined by an electrolyte and separated fromthe sample by a membrane of the same type discussed previously in connection with the $PCO_2$ sensor. A suitable polarizing voltage is applied across the electrodes whereupon oxygen diffusing from the sample through the membrane into the electrolyte will be reduced at the cathode, thus producing a change in output current of the cell which is indicative of the partial pressure of oxygen in the sample.

An important feature of the present invention is to seaprate the measuring electrodes and the reference electrodes of the $PCO_2$ and$PO_2$ measuring cells and to use a single reference electrode 238 which is common to the $PCO_2$ and $PO_2$ measuring electrodes as well as to the pH measuring electrode. Thus, in accordance with the invention the $PCO_2$ measuring electrode 16 comprises simply a glass electrode which is identical to the electrode 14, except that the ion sensitive glass bulb 240 is separated from sample passing through the sample passage 20 by means of a gas permeable essentially on impermeable membrane 242. This membrane is in the form of a circulAr disc which is positioned in the bottom of the bore 182. Preferably a liquid permeable pacer 244, formed of a suitable filter material or nyong mesh, for example, is disposed between the membrane 242 and the bulb 240 to provide a thin film pace herebetween. The electrode 16 is retained in the bore 182 by means of a sleeve 192 like that described previously in connection with the mountin means for electrode 14.

The $PO_2$ measuring electrode 18 comprises a nononductive body having a metal chathode therein terninating in a convex sensing end 246. This end is separated from sample in the passage 20 by means of a uitable gas permeable ion impermeable membrane isc 248. A thin electrolyte film space is provided between membrane 248 and sensing end 246 of elecrode 16. The membrane 248 is retained in the bottom of th ore 184 by a sleeve 192.

The three sleeves 192 are identical except that the leeves in bores 182 and 184 are provided with a pair of iametrically opposed openings 250. These openings xtend through the walls of the sleeves between te anges 194 and 202. A passage 254 in body 170 is ligned with openings 250 and interconnects the bores 182 and 184 to provide flow communication therebeween. The reference electrolyte container 236 is conected by means of a conduit 256 to a passage 258 in 1e body 170 of the flow cell. Passage 258 opens into 1e annular space defined between the flanges 194 and 02 of sleeve 192 in bore 182. As can be seen, each 2nsing electrode 16 and 18 is spaced slightly from the all of its corresponding mounting sleeve so that an nnular electrolyte flow path 260 is provided between 1e two elements which is in communication with the lm space between the membrane and sensing end of 1e electrode. By the aforementioned arrangement, it 1n be appreciated that the reference electrode 238 is 1 electrolytic communication with the aforementioned lm spaces provided for each of the electrodes 16 and 8. p Since ca common reference electrode 238 is used 1r all three measuring electrodes, the individual pH 1d $PCO_2$ measuring electrodes can be fabricated without a reference electrode in the same body and the $PO_2$ ectrode may be fabricated without an integral anode reference electrode. Thus, all three measuring elecodes may have the same configuration and be ounted in the flow cell by identical parts.

It can be appreciated thAt because a single electrote is employed for providing communication between ference electrode 238 and the measuring electrodes l, 16 and 18, the electrolyte must embody the necesry constituents for proper operation of each of the easuring electrodes. This requres that the ellectrolyte container 236 contain a suitable salt, preferably KCl, well as bicarbonate for the $PCO_2$ measuring elecode.

Another important feature of the invention is the oviding of means for flushing the capillary liquid nction 234 between the measuring electrodes 14, 16 id 18 and the reference electrode 238. Liquid junc)ns for pH electrodes have caused many problems in e past since the junctions must be made directly to e sample. Some of the most serious problems of in:umentation of the type to which the present inven)n applies has been either contamination of the liquid nction, too high a electrolyte flow rate, or discontinues in the flow of reference solution. When the liquid junction becomes contaminated by either sample or buffer solution, junction potentials arise when analyzing the sample orbuffer. These problems are avoided in the present invention by providing a porous plug 261 between the capillary liquid junction 234 and the reference electrode 238 and a bypass for the plug. The plug, which may be formed of a porous ceramic, is positioned in a conduit 262 connected at one end to the outlet end of the capillary opening 234. The other end of conduit 262 is connected to a passage 264 in the flow cell body 170. This passage opens into the bore 184 in alignment with the openings 250 in the mounting sleeve in the bore. The porous plug 261 serves as a means of providing a low flow-low resistance path with sufficient impedance to back pressure to prevent the sample in passage 20 from contaminating the plug. In order to flush the liquid junction opening 234, a bypass line 266 is connected at opposite ends into the conduit 262 on opposite sides of the plug 261. A pump 268 in the line 266 may be momentarily energized to bypass the plug 261 with electrolyte solution from container 236 so that junction 234 can be periodically flushed with fresh electrolyte solution. Sample flushed from the capillAry passage 234 will exit from the flow cell through the outlet port 232.

Since a common remote reference electrode 238 is employed in the present invention, there may be utilized a large electrolyte reservoir 236 which will contain a sufficient amount of electrolyte solution to assure that a supply of electrolyte will be available over a long period of time for the gas measuring electrodes 16 and 18. This will avoid the necessity of having an operator disassemble these electrodes frequently from the flow cell to recharge the electrodes with additional electolyte as is the practice with present analyzers employing conventional $PCO_2$ and $PO_2$ measurin cells consisting of two elecrodes each in a single body. Also, because the present invention employs a single remote reference electrode 238, a conventional reference electrode may be used which has a large volume of internal KCl electrolyte solution with the same concentration of KCl as conatined in the eklectrolyte vessel 236 thereby providing a highy stable junction potential. In addition, since only a single reference electrode is employed, the problem existent in prior multiple electrode assemblies of maintaining each reference elecrode at the same temperature is also overcome. These advantages can also be achieved by using a common remote reference ellectrode with conventional $PCO_2$ and $PO_2$ sensors by not connecting the integral reference electrodes of such sensors to the readout apparatus and by providing electrolytic communication between the remote reference electrode and the measuring electrodes in such sensors.

Another novel feature of the invention is the provision of a unique sample passage through the flow cell 20 which will allow low sample volumes, minimal pressure differentials and intimate contact between the sample and all active areas of the sensing electrodes but prevent bubble entrapments about the sensing electrodes. This is achieved by providing three concave wells 270 in the lower section 174 of the flow cell body 170, These wells open at the upper surface 272 of the lower section 174 in alignment with the bores 180, 182 and 184 in the upper section 178. The configuration of the wells 270 is essentiallly identical to the configuration of the convex sensing ends 188 of the measuring electrodes 14, 16 and 18 so that there is provided therebetween a small sample space 274 uniform depth. The inlet section 276 of the sample passage 20 for each respective well 270 extends upwardly at an angle of about 45° and enters at the bottom of the well while the outlet section 278 of the sample passage for each respective well extends downwardly from the upper portion of the well at an angle of about 60° from the vertical plane. The outlet section 278 of the wells associated with the measuring electrodes 14 and 16 are connected to the inlet sections 276 of the two wells downstream thereof, while the last outlet section 278 is connected to the outlet port 232 of the sample passage. Thus, sample flowing through the sample passage 20 will enter at the bottom of each well, flow up and around the convex sensing end of the measuring electrode and leave at the top of the well. The sample will flow through the cell 12 in a continuousmanner in intimate contact with te sensing end of each of the measuring electrodes with minimal pressure differentials and essentially no bubble entrapment. Because of the short path length of the sample passage and the novel configuration of the passage discussed above, sample volumes as small as 90 microliters may be employed in the flow cell of the present invention.

Figure 9:
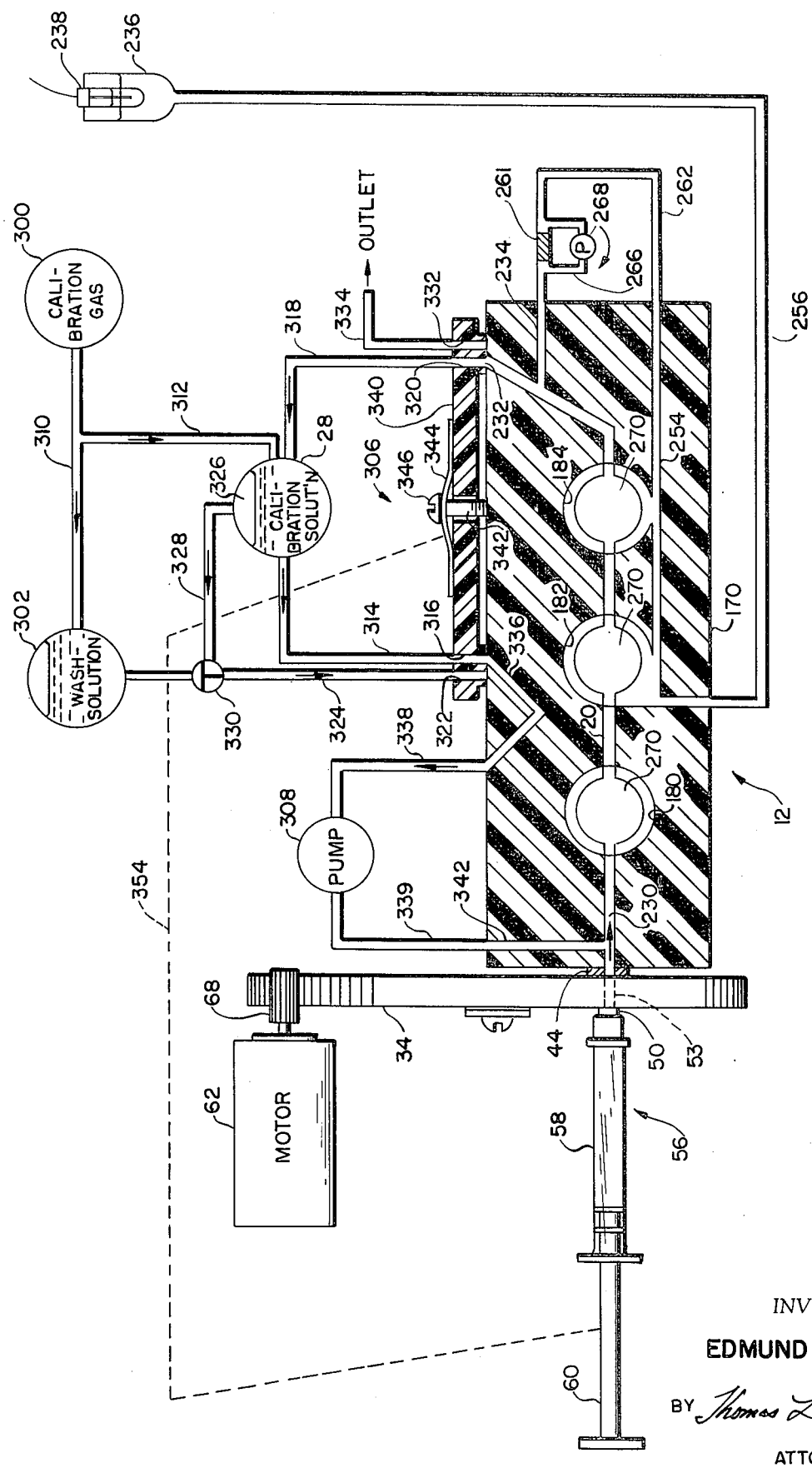
FIG. 9 is a schematic illustration of the apparatus of the present invention.

Reference is now made to FIG. 9,wherein there is schematically illustrated the flow cell 12 of the present invention together with the various components employed for facilitating the passage of a calibration solution and wash solution through the sample passage 20 in the cell. Such components include a tank 300 for holding a calibration gas, a vvessel 302 for holding a wash solution, the vessel 28 for holding a calibration solution, a valve assembly 306 mounted on the side of the flow cell body 170, and a pump 308. A conduit 310 connects the tank 300 to vessel 302 while conduit 312 connects the tank to the vessel 28. A conduit 314 connects vessel 28 to one port 316 in the valve assembly 306 while a conduit 318 connects vessel 28 to another port 320 in the valve assembly. The wash solution vessel 302 is connected to still a further port 322 in the valve assembly by means of a conduit 324. The head space 326 of the calibration solution vessel 28 is connected to the conduit 324 by a further conduit 328. A normally open solenoid valve 330 is located at the junction of the conduits 324 and 328 and is normally positioned to allow flow communication between te head space 326 of vessel 28 and the port 322 in the valve assembly. A fourth port 332 in the valve assembly is connected to a waste conduit 334. A passage 336 is provided in the body 170 having one end in registry with the port 316 inthe valve assembly 306 and its other end connected by means of conduit 338 to the inlet of the pump 308. The outlet of the pump is connected by conduit 339 to a passage 342 which engages the sample passage 20 just beyond its inlet end 230. When the valve assembly 306 is in its normal position, the calibration solution vessel 28 is in flow communication with the inlet of pump 308 by means of conduit 314, port 316 and passage 336 and the outlet 232 of the sample passage 20 is in flow communication with vessel 28 via the port 320 in the valve assembly and conduit 318. When the valve assembly 306 is shifted to a second position, port 322 is brought into registry with the passage 336 and the port 332 is brought into registry with te outlwt end 232 of sample passage 20.

Figure 11:
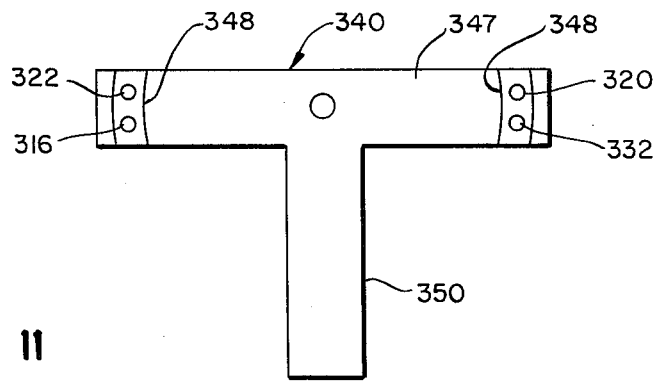
FIG. 11 is a side elevational view of the inner face of the valve element illustrated in FIG. 10.
Figure 10:
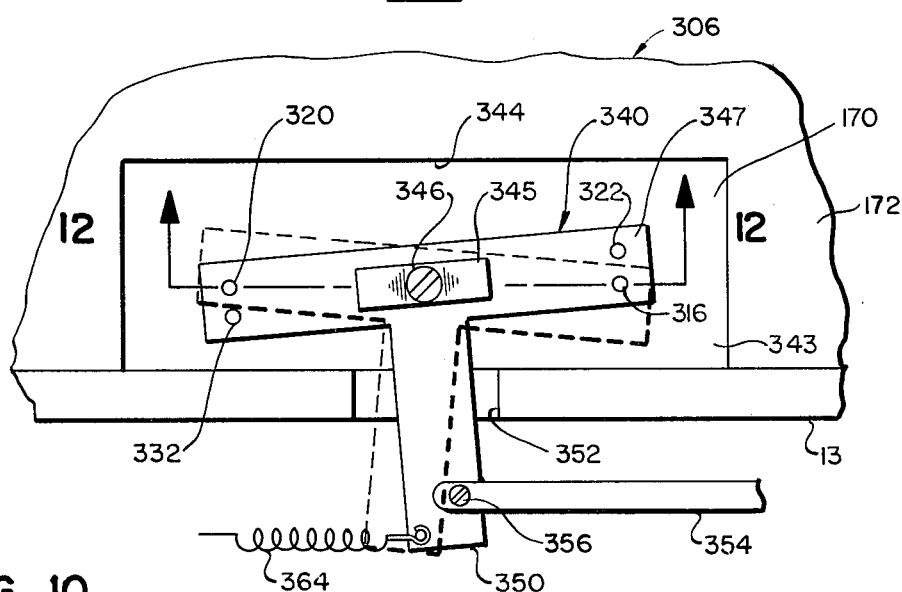
FIG. 10 is a vertical sectional view taken along line 10—10 of FIG. 3 illustrating the valve assembly employed on the flow cell of the apparatus with the connecting conduits omitted for clarity.
Figure 12:
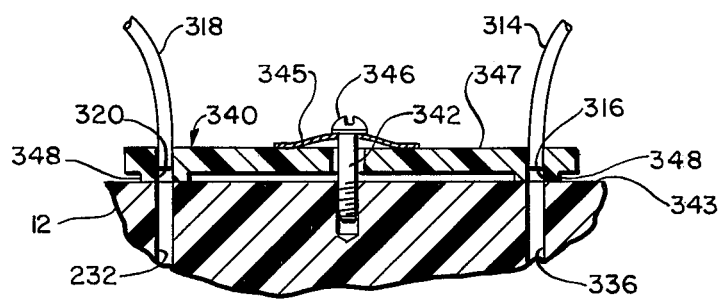
FIG. 12 is a horizontal sectional view taken along line 12—12 of FIG. 10 showing two conduits connected to the valve assembly.

Reference is now made to FIGS. 10–12 which illustrate in detail the actual structure of the valve assembly 306. The valve assembly comprises a T-shaped valve element 340 which is pivotally mounted by a screw 342 to a side 343 of the flow cell boey 170 which is exposed through an opening 344 in the metal housing 172. A leaf sprin 345 is positioned between the head 346 of the screw and the outer surface of the valve element 340 to urge the valve element toward the side 343 of the body.

The cross piece 347 of the T-shaped valve element 340 is provided on its inner face adjacent to each end with an outwardly projecting segment 348 of an annular ring which engages the side 343 of the body 170. The passages 322 and 316 pass through one of the projections 348 while the openings 320 and 332 pass through the other projection. Such projections are preferably formed of a self-lubricating material such as Teflon which will slide easily on the side 343 of the flow cell body.

The lower end 350 of thevalve element 340 extends through a vertical slot 352 in the base 13. A rod 354 is pivotally mounted to the lower end 350 of the valve element by means of a pin 356. The opposite end of the rod 354 passes through an opening 358 in a bracket 360 affixed to the lower part 98 of syringe drive block 90 as best seen in FIGS. 3 and 4. The opening 358 is sufficiently large to permit the rod 345 to freely slide therein. An enlarged head 362 is provided at the end of the rod 354 behind the bracket 360. A spring 364 is connected at one end to the lower end 350 of the valve element 340 and at its opposite end to a post 366 affixed to the bottom of base 13. With the syringe drive block 90 located in its rearwardmost position within the slot 92 in base 13, the bracket 360engaging head 362 on rod 354 holds the valve element 340 in the position illustrated in FIG. 10 wherein the passage 320 is in registry with the outlet end 232 of the sample passage and passage 316 is in registry with the passage 336 in the flow cell. When the syringe drive block 90 advances forwardly to remove the bracket 360 from the head 362 on the rod 354, the spring 364 will shift the valve element 340 to the position shown in phantom lines in FIG. 10 wherein port 332 in thevalve element is in registry with the outlet end 232 of the sample passage and port 322 is in registry with the passage 336. The valve element will remain in such phantom line position until the block 90 returns to the rear of slot 92 whereupon the bracket 360 will engage the head 362 on rod 354 thereby returning the valve element 340 to the position shown in full lines in FIG. 10.

Thus, when the valve element 340 is positioned as shown in full lines in SIGS. 9 and 10, the calibration solution from vessel 28 will be recirculated through the flow cell by means of the pump 308..

The calibration solution contained in vessel 28 consists of physiologically normal concentrations of sodium, potassium, chloride and bicarbonate ions. The wash solution contained in vessel 302 contains surface active agents to condition the sample passage and any other agents required to clean the passage, such as enzymes or heparin. The tank 300 contains a physiological normal gas partial pressure of carbon dioxide and oxygen. Since the tank 300 is connected to vessels 28 and 302 by conduits 312 and 310, respectively, both the wash solution and cilbration solution are constantly equilibrated with the physiologically normal gas from tank 300. Since the bicarbonate ion concentration of the calibration solution 28 is known as is the partial pressure of $CO_2$ in the calibration gas, the pH of the solution may be determined by the familiar Hendersen-Hasselbach relationship. Thus, a single calibration fluid is provided which permits simultaneous calibration of the pH, $PCO_2$ and $PO_2$ measuring electrodes in the flow cell when the solution is circulated therethrough. Since the vessel 28 is mounted in the flow cell 12, the calibration solution will be maintained at the same temperature as the sample flowing through the cell by the heating elements 22 and 24. Hence, a highly reliable, reproducible and stable method of calibration is achieved for all the measuring electrodes using only a single solution. This method of calibration circumvents the conventional procedures requiring carefully controlled humidified gases at constant temperature for $PCO_2$ and $PO_2$ calibration and separate buffers and standards for pH ccalibration. Moreover, since a liquid is used as the calibrating media, the calibration conditions closely approximate the actual conditions of measuring the blood sample itself.

When the valve element is shifted to the phantom line position illustrated in FIG. 10, and when the solenoid valve is in its normal position as shown in FIG. 9, physiological normal gas from head space 326 of vessel 28 will be conveyed by the pump 308 through conduits 328 and 324 into sample passage 20 to purge any liquid remaining in the passage outwardly through passage 332 in the valve element to the waste conduit 334. On the other hand, when the solenoid valve 330 is energized to bring the wash solution vessel 302 into flow communication through conduit 324 with the flow cell, wash solution will be carried by the pump 308 through the sample passage to clean the same. Since the wash solution and calibration solution are both continuously equilibrated by the calibration gas in tank 300, the measuring electrodes in the flow cell will be continuously subjected to a fluid having a physiological normal partial pressure of carbon dioxide and oxygen regardless of whether the calibration solution, wash solution, or gas from the head space above the calibration solution is flowing through the sample passage. This arrangement avoids substantial changes in the output signals of the $PCO_2$ and $PO_2$ electrodes, and thus delay in analyssis of samples, which would otherwise occur if merely atmospheric air or normal wash solutions were passed through the flow cell.

Figure 13:
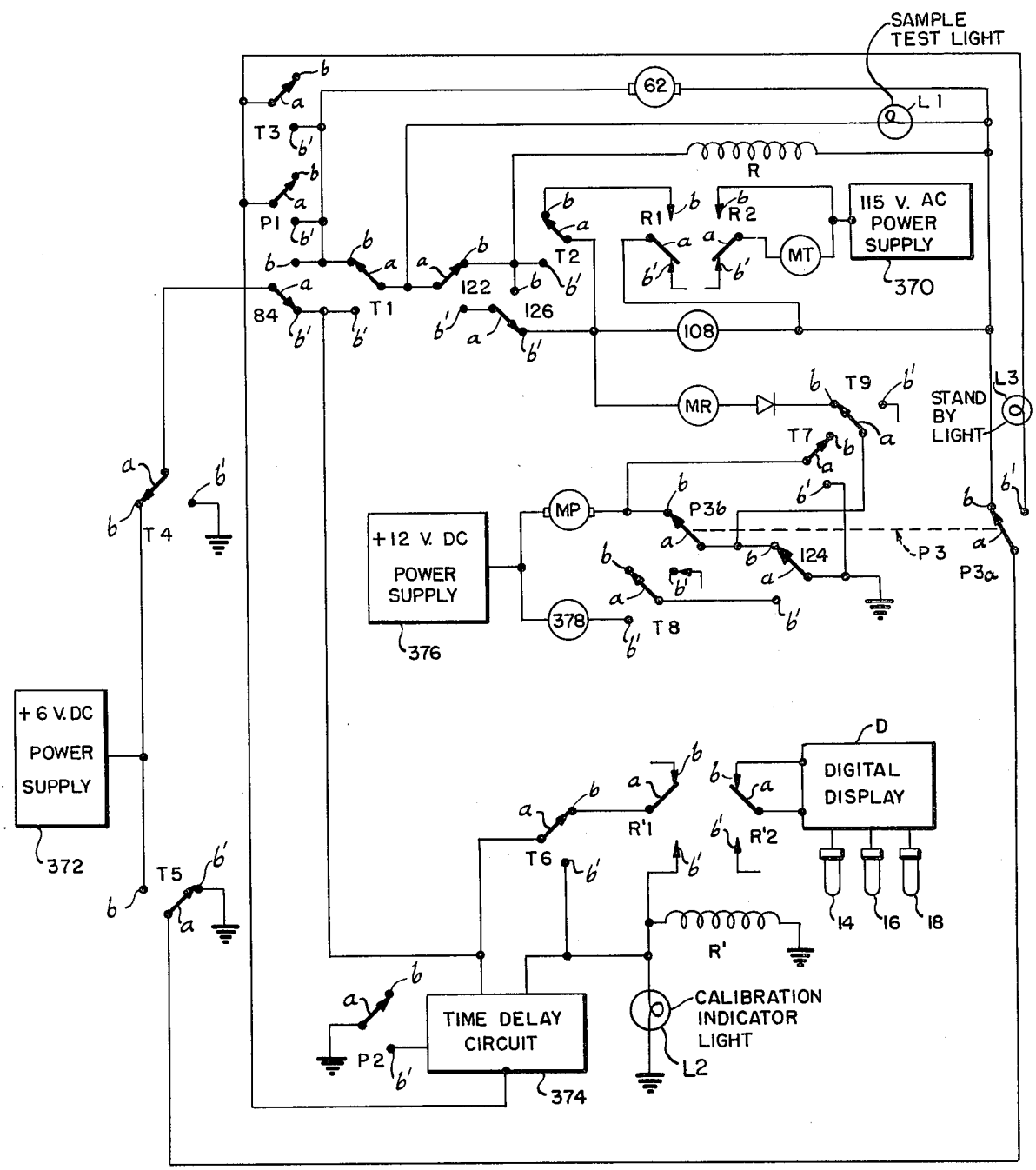
FIG. 13 is a diagram of the control circuit employed in the apparatus of the invention.

The overall operation of the present inventio can best be appreciated by making reference to FIG. 13 which illustrates an exemplary control circuit for the apparatus. As indicatedpreviously, a sample is initially obtained from a patient by the use of a conventional commercial disposable syringe. The needle from the syringe is removed and the syringe cylinder 58 is attached to the Luer-lock 50 on circuular disc 34.

The control circuit is controlled by a timer, not shown, driven by a timer motor MT which activates nine mechanical switches T1–T9 in a series of 60 steps. The motor MT is powered by a 115 volt a.c. source 370. A 6 volt d.c. power supply 372 is provided for energizing relays R and R', motors 62 and 108, a motor MR which drives pump 268, and a time delay circuit 374, while a 12 volt d.c. source 376 is provided for energizing a motor MP which drives the pump 308, and a solenoid 378 which operates valve 330. The circuit also includes two manually operable momentary switches P1 and P2 and a double pole-double throw latching switch assembly P3 consisting off switches P3 and P3b. Switch P1 is operable to energize the motor 62. Switch P2 is oprable to energize the time delay circuit 374 which serves to allow time for the measuring electrodes to equilibrate with the calibration solution. Operation of switch P1 or P2 serves to unlock switch P3. Switch assembly P3 is operable to stop all functions at any desired time in the sequential operations performed. Microswitch 84 also serves to control the supply of power to the motor 62, while the switches 122, 124 and 126 are operable by the rod 134 carried by te syringe drive block 90 to control various functions of the apparatus as will be seen later. The relays R and R' are operable for actuating a pair of relay switches R1, R2 and R1', R2', respectively. Each of the switches included in the circuit includes a movable arm designated a which is cooperative with a pair of fixed contacts b and b'. The circuit also includes a sampl test light L1 operable by switch P1, a calibration indicator light L2 operable by switch P2 and a standby light L3 operable by switch assembly P3.

FIG. 13 shows the control circuit in a normal condition when the apparatus is in a ready state for either calibration or the testing of a sample. In this condition, the movable arm a of switch T1 engages fixed contact b and the movable arm a of switch P1 engages contact b so that no power is supplied from the source 372 to the motor 62. The motor MP, however, is energized from the source 376 through switches P3b and 124. Motor MP driving the pump 308 causes calibration solution to be circulated through the sample cell 12 so that at this time the apparatus may be calibrated if desired. To perform an analysis of a sample which is contained in the syringe 56 connected to the wheel 34, the operator manually shifts movable arm a of switch P1 to engage fixed contact b' so that power is applied from the 6 volt supply 372 through switch P1 to the motor 62 which rotates the wheel 34 in a clockwise direction as viewed in FIG. 5. At this time, six volts are also supplied through switches P1, T1 and 122 to relay R to energize the same. Energization of the relay R causes the arm a of switch R2 to engage contact b of the switch thereby closing the circuit between th 115 volt alternating current sources 370 and motor MT. This effects energization of motor MT causing the tinmer, not shown, to move through the sixty steps mentioned previously.

In step 1 of the timer, the arm a of switch T1 is shifted to engage contact b'. Simultaneously, as the wheel 34 driven by the motor 62 is rotated, the arm a of switch 84 comes into engagement with fixed contact b of the switch. This occurs because the tab 80 carried by the wheel 34 moves away from the actuating arm 82 of switch 84 thereby permitting the switch to close. Thus, at this instance power is supplied from the 6 volt source 372 to the motor 62 through both the switches P1 and 84. Also, power to the relay R is cut off and therefore the timer motor MT is de-energized. Thus, only momentary contact of the push button P1 is required by the operator to set the circuit into operation, permitting the motor 62 to rotate wheel 34 thereby bringing the syringe 56 into alignment with the sample passage in the cell.

After the wheel 34 reaches its lower limit, the tab 78 on the wheel causes the arm a of switch 84 to be shifted to engage fixed contact b' thereby de-energizing the motor 62 and stopping rotation of the wheel 34. At this time, however, power is again supplied now from the source 372 through switches 84, T1 and 122 to the relay R. Energization of the relay causes the arm a of relay switch R2 to engage fixed contact b of the switch and again supply power to the timer motor MT which starts to rotate the timer through its subsequent steps.

When the timer motor has advanced the timer to its third step, power continues to be supplied from the source 372 to the relay R through switches 84, T1 and 122. The arm a of switch T2, however, is now brought into engagement with contact b' of the switch to supply power through switches 84, T1, 122 and T2 to the syringe drive motor 108 and MR which drives the pump 268 thereby supplying potassium chloride solution from reservoir 236 through the capillary passage 234 in cell 12 to flush the same. As the syringe drive 85 begins to advance by virtue of the motor 108 being energized, the valve 306 is shifted, in the manner described previously, to switch the intake of the pump 308 from the calibration solution to the calibration gas supplied from the top of the reservoir 28 and the outlet 232 of the sample cell is connected to the waste outlet 334. Since the pump motor MP is still operating at this time, any calibration solution remaining in the sample passage 20 will be expelled to waste by the calibration gas conveyed by the pump 308 through the sample passage.

When the syringe drive begins to advance, switch actuating rod 134 carried by the syringe drive block 90 immediately shifts arm a of switch 122 to engage fixed contact b so that power will continue to be supplied to syringe drive motor 108 and motor MR through switches 84, T1, 122 and 126.

Whem the timer advances the timer to its fourth step, the arm a of switch T2 engages fixed contact b and motors 108 and MR will continue to be energized through switches 84, T1, 122 and 126. As the syringe drive continues to advance, the rod 134 on the drive will actuate switch 124 shifting its movable arm a into engagement with its respective fixed contact b'. When this occurs, power to the pump motor MP is also interrupted and the pump 308 ceases functioning. The power to motor MR is also interrupted at this point and thus the pump 268 ceases to supply potassium chloride electrolyte to the capillary junction 234. The syringe drive, however, continues to advance until the sample syringe is engaged by post 116 on the syringe device and the sample has been completely injected from the syringe cylinder 58 into the sample passage 20 of cell 12. At this point, the rod 134 of the syringe drive actuates switch 126 bringing its arm a into engagement with fixed contact b. The syringe motor 108 is then de-energized. At the same time, power is now applied through switches 84, T1, 122 and 126 to relay R which lifts arm a of relay switch R2 into engagement with corresponding fixed contact b to again energize the timer motor MT. At the same time the arm a of relayswitch R1 rises to engage contact b which provides a short from each side of the syringe drive motor 108 thereby acting as a brake for this motor.

The only event occurring as the timer goes to step 5 is to move arm a of switch T9 so as to engage fixed contact b'. This event is of no consequence at this moment. The timer then continues to advance from steps 5 through 49 requiring a period of approximately 67 seconds which allows the sample row in the cell 12 to come to equilibrium with the measuring electrodes 14, 16 and 18 in preparation for readout of the electrodes. At position 50, the timer shifts the arm a of switch T6 to engage its respective fixed contact b' so that power from the 6 volt supply 372 will now be applied to relay R' through switches 84 and T6. Energization of this relay pulls the arms a of relay switches R1' and R2' into engagement with fixed contacts b' of the switches. This unlocks a memory circuit, not shown, in a digital display unit D thereby removing the display of the output of the measuring electrodes 14, 16 and 18 resulting from the analysis of the previous sample, and allowing display of the output of the measuring electrodes for the sample presently being analyzed.

Advancing of the timer to step 51 allows additional time for equilibrium to be reached between the measuring electrodes and the sample and for their readout signals to be stabilized on the display D. In step 52 of the timer, arm a of switch T6 is returned to fixed contact b thereby removing power from the relay R' and again clamping the display D to lock in its memory circuit. When this occurs the values of the various parameters of pH, $PO_2$ and $PCO_2$ from the measuring electrodes will be held in a locked position.

In step 53, the timer shifts arm a of switch T7 so as to engage fixed contact b' thereby closing the circuit between the power supply 372 through the motor MP and switch T7 to ground. The motor MP is thereby energized to activate the pump 308 whereby gas from the top of the calibration solution reservoir 28 will be conveyed through the sample passage of the cell 12 to waste, forcing the sample out of the cell. Step 54 of the timer allows an additional period of time for this gas pruging of the cell.

When the timer reaches step 55, the arm a of switch T8 is brought into engagement with fixed contact b'. When this occurs solenoid 378 associated with the valve 330 is energized. As stated previously, in the normal position of the valve 330 gas from the top of the reservoir 28 is supplied to the inlet of the pump 308. Energization of the solenoid 378 shifts the valve 330 so as to cut off such supply of gas and allow wash solution from the container 302 to be pumped through the cell by the pump 308, thereby flushing the cell of any sample contained therein. At this same step 55 of the timer, the arms a of switches T4 and T5 are shifted so as to engage their respective fixed contact b' thereby reversing the polarity of the 6 volt source 372 supplied to the circuit so that all motors in the circuit will operate in a reverse direction.

As the timer moves to step 57, the arm a of switch T2 is brought into engagement with fixed contact b' of the switch so that 6 volts are again supplied to the syringe motor 108, however in a reverse direction, throgh switches T2, 126, 122, T1 and 84. The syringe motor drive now begins to pull the syringe plunger 60 out of the cylinder 58, and at the same time the pump 308 supplies wash solution through the cell 12 in sufficient quantity to both purge to waste any material remaining in the sample passage 20 and to fill the syringe cylinder as the plunger is withdrawn.

At step 58, the timer shifts the arm a of switch T2 to engage fixed contact b of the switch so that power is then cut off from the timer motor MT. The syringemotor 108, however, remains energized through switches 126, 122, T1 and 84. As the syringe drive mechanism continues in a rearward direction the switch actuating rod 134 carried by the syringe drive block 90 again actuates switch 126 causing the arm a of the switch to engage fixed contact b' thereof. This allows the motor 108 to continue operation even after switch T2 has changed position as just described. Also, during return movement of the syringe drive the switch 124 is actuated to return its arm a into engagement with fixed contact b. At this poit, power is cut off from the solenoid 378 so that the valve 330 will return to its normal position allowing gas to flow from the head space 326 in the vessel 28 to the input of the pump 308 so that any wash solution in the cell 12 will be purged therefrom to waste. The syringe cylinder 58 at this time is filled completely with wash solution and the syringe drive is released from the head 119 of the syringe. As the syringe drive continues to its rearwardmost position, the rod 134 actuates the switch 122 to xause its arm $a$ to engage fixed contact $b$ thereof. When this occurs, power is cut off from the motor 108 and power is again supplied to the relay R whereby the arms $a$ of switches R1 and R2 are brought into engagement with their respective fixed contacts $b$, theby activating the timer motor TM and providing a shunt across the motor 108 to act as a brake. Also, as the syringe drive returns to its rearwardmost position, the bracket 360 carried by the syringe block 90 will engage the head 362 on the rod 354 to return the valve element 340 to the position illustrated in FIG. 10 so that now calibration solution may be supplied to the sample cell 12. Since the pump motor MP is still energized, the calibration solution will be continuously circulated through the cell. When the timer reaches step 59, the arm $a$ of switch T3 comes into engagement with fixed contact $b'$ to thereby apply power from source 372 again to the motor 62, in a reverse direction through switch T3. The motor rotates the disc 34 in a counterclockwise direction as viewed in FIG. 7 until it returns to the position illustrated in FIG. 5. As the wheel commences to rotate the tab 78 disengages from the actuating arm 82 of switch 84 thereby causing the movable arm $a$ of the switch to engage fixed contact $b$ of the switch thereby providing an additional path for power from source 372 to the motor 62.

In step 60 of the timer, the arm $a$ of switch T3 lifts off the fixed contact $b'$ and power continues to be supplied to the motor 62 through switch 84. At this time the arm $a$ of switch T1 is shifted into engagement with fixed contact $b'$ which cuts off the power to the relay R and stops the timer motor MT. When the motor 62 has advanced the disc 34 to the position illustrated in FIG. 5, wherein the syringe is in its "up" position, the tab 80 again actuates switch 84 to shift arm $a$ into engagement with contact $b'$ which cuts off power to the motor 62, but again supplies power to relay R through switches S1, T1 and 84, lifting the arms a of relay switches R1 and R2 into contact with their respective contacts $b$, causing the timer motor to again advance. The motor MT will advance the timer from step 60 to step 1. At this time switches T1, T4, T5, T7, T8 and T9 are actuated to return the circuit to its initial condition as shown in FIG. 13, wherein the foregoing sequence of steps may be repeated for analysis of additional sample.

While the sample determination sequence is being performed, the sample test light L1 is illuminated. When switch P2 is depressed, the calibration may be performed if, or after the calibratin solution has been circulating for a predetermined time, preferably 60 seconds, as determined by the time delay circuit 374. During the calibration, at which the display D is active, the calibration light L2 is illuminated. By operating switch P3, the instrument may be held at any particular function during the sample determination sequence. This is useful, for instance to provide an extra length of time for initially establishing the liquid junction, establishing sample equilibrium, purging, or washing the system. When switch P3 is depressed, the standby light L3 is illuminated. To return the instrument to its normal mode, switch P1 or P2 is depressed which immediately overrides switch P3.

From the foregoing, it can be appreciated that by the present invention there is provided an automated analyzer which permits rapid, reliable and economical analysis of liquid or gas samples. The apparatus requires no more operator attention than merely securing a conventional syringe to the disc 34. Since the sample is positively displaced from the syringe cylinder by an automatic and repeatably operating syringe drive mechanism, sample will be introduced within the flow cell at a constant rate under repeatable conditions of velocity and minimal pressure, thus avoiding introduction of air or gas bubbles within the cell or sudden pressure differentials. Because of the particular design of the sample passage in the flow cell, bubble entrapment is avoided about the measuring electrodes and purging and cleaning of the sample passage is facilitated.

The use of a single reference electrode in the present invention which is common to all the measuring electrodes greatly simplifies manufacture and maintenance of the apparatus. The mounting of the reference electrolyte container remote from the flow cell also permits the use of a large supply of electrolyte solution which will prevent the $PO_2$ and $PCO_2$ electrodes from drying out. Moreover, by the use of a calibration solution which contains physiological normal concentrations of sodium, potassium, chloride and bicarbonate ions, and which is constantly equilibrated with physiological normal partial pressure of carbon dioxide and oxygen, the pH, $PCO_2$ and $PO_2$ measuring electrodes may be calibrated simultaneously, thereby providing a highly accurate means of calibration, and a savings in time of operation of the apparatus as well as in manufacturing costs.

It will be appreciated that various modifications may be made in the apparatus 10 without departing from the present invention. For example, the disc 34 to which the sample syringe 56 is attached could be manually rotated to bring the syringe into registry with the sample passage 20 in the flow cell rather than using the motor 62 to perform this function automatically. In addition, the disc 34 could be eliminated and the syringe 56 could be mounted directly to the flow cell in registry with the sample passage. Also, the flow cell might incorporate only ion measuring electrodes, for example sodium or potassium ion measuring electrodes, in addition to the pH electrode 14, or alternatively the pH electrode could be eliminated and only gas measuring electrodes might be employed in the flow cell. In either case, calibration of the flow cell would be simplified as will be apparent to one skilled in the art.

Although only a single embodiment of the invention has been disclosed herein in detail for purposes of illustration, it will be appreciated that various changes in addition to those just mentioned can be made in the form, details, arrangement and proportions of the various parts in such embodiment without departing from the spirit and scope of the invention as defined by the appended claims.

What is claimed is:

1. A flow cell assembly containing ion measuring and gas sensitive sensors for electrochemical analyses, said assembly comprising:
   a body of insulating material having a sample passage extending therethrough;
   an ion measuring electrode mounted in said body and havin an ion sensing end positioned to contact sample flowing through said passage;

a gas sensitive electrode including a sensing end mounted in said body and a gas permeable essentially ion impermeable membrane separating said sensing end from sample flowing through said passage, said membrane being spaced from said sensing end to provide therebetween an electrolyte film space;

a reservoir containing a reference electrolyte for said gas sensitive electrode;

electrolyte communicating passages between said reservoir and said film space and said sample passage; and an electrode mounted in said reservoir, said last mentioned electrode combining with said ion measuring electrode to define said ion measuring sensor and combining with said gas sensitive electrode to define said gas measuring sensor in said assembly.

2. A flow cell for electrochemical analyses comprising:

a body of insulating material having a sample passage extending therethrough;

a reference electrode in electrolytic contact with sample flowing through said passage and also in electrolytic contact with one or more electrolyte solutions each separated from said sample by a gas permeable essentially ion impermeable membrane;

one or more ion measuring electrodes in contact with said sample; and a gas measuring electrode in each of the electrolyte solutions separated from said sample by an associated membrane, each gas measuring electrode being spaced from the associated membrane to provide an electrolyte film space therebetween.

3. A flow cell assembly comprising:

a body of insulating material having a sample passage extending therethrough;

a potentiometric-type gas measuring sensor and a polarographic-type gas measuring sensor for measuring different gases flowing in said sample passage and each including and sharing a common reference electrode mounted in a reservoir containing a reference electrolyte comprising a combination of electrolytes for said potentiometric and polarographic sensors, said potentiometric sensor further including a hydrogen ion sensitive electrode mounted in said body and a gas permeable essentially ion impermeable membrane separating a sensing end of said hydrogen ion sensitive electrode from sample flowing through said passage, said membrane being spaced from said sensing end to provide therebetween an electrolyte film space, and said polarographic sensor further including a metal cathode mounted in said body and a separate gas permeable essentially ion impermeable membrane separating a sensing end at said metal cathode from sample flowing through said passage, said separate membrane being spaced from said sensing end of said metal cathode to provide therebetween a separate electrolyte film space; and electrolyte communicating passages between said reservoir and said film spaces and said sample passage.

* * * * *